(12) United States Patent
Miller

(10) Patent No.: US 9,021,862 B2
(45) Date of Patent: May 5, 2015

(54) NH3 STORAGE SETPOINT TEMPERATURE ALGORITHM

(71) Applicant: Michael James Miller, Mt. Prospect, IL (US)

(72) Inventor: Michael James Miller, Mt. Prospect, IL (US)

(73) Assignee: International Engine Intellectual Property Company, LLC., Lisle, IL (US)

( * ) Notice: Subject to any disclaimer, the term of this patent is extended or adjusted under 35 U.S.C. 154(b) by 0 days.

(21) Appl. No.: 14/047,113

(22) Filed: Oct. 7, 2013

(65) Prior Publication Data

US 2015/0096350 A1 Apr. 9, 2015

(51) Int. Cl.
*G01N 25/00* (2006.01)
(52) U.S. Cl.
CPC ...................................... *G01N 25/00* (2013.01)
(58) Field of Classification Search
CPC .................................................. G01K 2213/00
See application file for complete search history.

(56) References Cited

U.S. PATENT DOCUMENTS

| 5,781,877 A | * | 7/1998 | Rachel et al. ............... 73/114.68 |
| 2002/0044897 A1 | * | 4/2002 | Kakwani et al. .............. 422/172 |
| 2008/0034738 A1 | * | 2/2008 | Singh et al. ..................... 60/295 |
| 2012/0020854 A1 | | 1/2012 | Makartchouk et al. |

* cited by examiner

*Primary Examiner* — Laura Martin
*Assistant Examiner* — Alex Devito
(74) *Attorney, Agent, or Firm* — Jeffrey P. Calfa; Mark C. Bach

(57) ABSTRACT

A method for predicting an exhaust gas temperature. The method includes detecting a plurality of exhaust gas temperatures and applying a weight value to the detected plurality of exhaust gas temperatures to determine a plurality of weighted temperature values. The weight value applied to at least one detected exhaust gas temperature may be different than the weight value applied to at least one other detected exhaust gas temperature. The method also includes determining an estimated temperature corresponding to the plurality of weighted temperature values and the applied weight value. The estimated temperature may be used to determine a set-point for the storage or absorption of a reductant by a catalyst. Moreover, the estimated temperature may allow for an adjustment to the reductant being stored on the catalyst if the storage capacity of the catalyst may be changing based on a predicted change in exhaust gas temperature.

4 Claims, 3 Drawing Sheets

NH3 STORAGE SETPOINT TEMPERATURE ALGORITHM

BACKGROUND

Combustion engines may employ emission controls or systems that are configured to reduce the amount of nitrogen oxides ($NO_x$), such as nitrogen dioxide, present in the engine's exhaust gas. One aspect of controlling such emissions may include the use of a NOx particulate filter (NPF) that has a Selective Catalytic Reduction (SCR) system and a particulate filter, such as a diesel particulate filter (DPF). The particulate filter is configured to remove particulate matter, such as soot, from the exhaust gas. The SCR typically uses a SCR catalyst, which, in some designs, may be coated on the particulate filter, and a reductant to convert NOx in the exhaust gas into nitrogen gas and water. Typically, the reductant is injected or dosed into the exhaust gas before the exhaust gas enters the NPF. The reductant may be a liquid or gas, such as, for example, ammonia ($NH_3$), among others. At least a portion of the reductant that is injected into the exhaust stream is absorbed onto the SCR catalyst where, with the assistance of the catalyst, the reductant reacts with the $NO_x$ in the exhaust gas to form water vapor and nitrogen. In order for $NO_x$ to be converted into nitrogen and water vapor, the SCR catalyst may be required to store an adequate amount of reductant.

The amount of reductant that the SCR catalyst is able to store or absorb may decrease as the temperature of the exhaust gases that encounter or are around the SCR catalyst increase. Accordingly, a set-point may be established, and adjusted during vehicle operation, that indicates the reductant storage capacity of the SCR catalyst. Moreover, such a set-point may be established in an attempt to prevent excessive amounts of reductant from being present in the exhaust gas stream, such as excessive amounts due to a reduction in the SCR catalyst's reductant storage capacity and/or through reductant dosing levels. The presence of excess reductant in the exhaust gas due to the reduced storage capacity of the SCR catalyst may result in, or increase the probability of, reductant slipping through the after-treatment system and wasting the reductant.

During certain operating conditions, the temperature of the exhaust gas may be elevated relatively rapidly. For example, a relatively quick and significant increase in engine load may result in a relative quick elevation in exhaust gas temperatures. Yet, such rapid elevation in temperature(s) may not allow for the time necessary for consumption of the stored reductant, an associated adjustment in the quantity of reductant that is to be stored on the SCR catalyst and/or an adjustment to the quantity of reductant that is being injected into the exhaust gas stream. In such situations, the decrease in the reductant storage capacity of the SCR catalyst may result in the presence of excess reductant in the exhaust gas that may, at least potentially, slip out of the after-treatment system wasting the reductant.

BRIEF SUMMARY

According to certain embodiments, a method is provided for predicting an exhaust gas temperature. The method includes detecting a plurality of exhaust gas temperatures and applying, by a control unit, a weight value to the detected plurality of exhaust gas temperatures to determine a plurality of weighted temperature values. The weight value applied to at least one detected exhaust gas temperature may be different than the weight value applied to at least one other detected exhaust gas temperature. The method also includes determining an estimated temperature corresponding to the plurality of weighted temperature values and the applied weight value.

Additionally, according to certain embodiments, a method is provided for predicting an exhaust gas temperature. The method includes detecting a plurality of exhaust gas temperatures and applying a weight value to the detected plurality of exhaust gas temperatures to determine a plurality of weighted temperature values. The weight value applied to at least one detected exhaust gas temperature may be different than the weight value applied to at least one other detected exhaust gas temperature. Further, the weight value may be based at least in part on the location of the detected exhaust gas temperature. The method further includes determining, by a control unit, an estimated temperature using a first summed value representative of the plurality of weighted temperature values and a second summed value representative of the weight values that were applied to the detected plurality of sensed temperatures.

DETAILED DESCRIPTION

Figure 1:
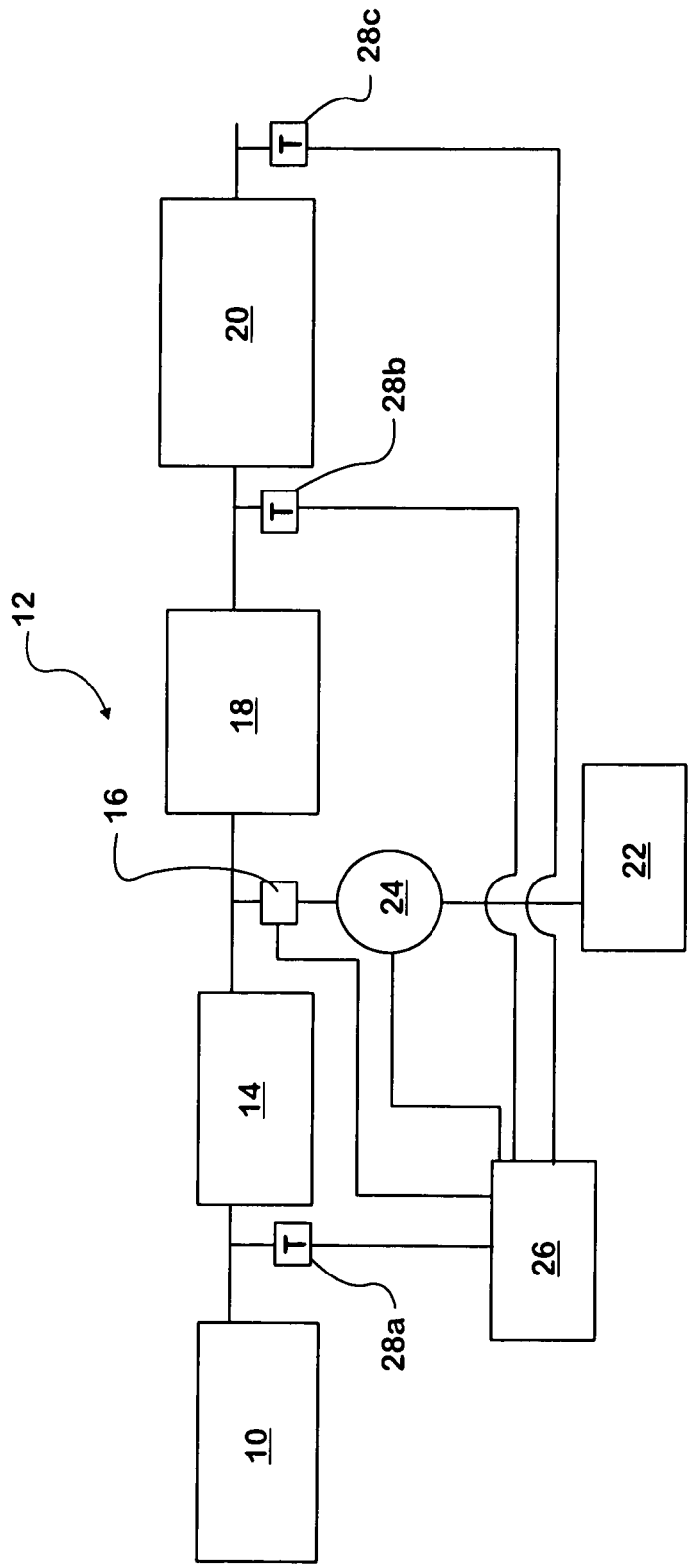
FIG. 1 illustrates an engine operably connected to an exemplary after-treatment system.

FIG. 1 illustrates an engine 10 operably connected to an after-treatment system 12. The illustrated after-treatment system 12 includes a diesel oxidation catalyst (DOC) 14, an injector 16 for injecting reductant, such as $NH_3$, into the flow of an exhaust gas, a mixer 18 for mixing the injected reductant and exhaust gas, and a NPF 20 having an SCR system. The SCR system of the NPF 20 may include an SCR catalyst that is used in the conversion of $NO_x$ into nitrogen and water vapor.

The reductant may be supplied to the injector 16 from a storage tank 22 via a pump 24. The amount of reductant injected or dosed into the exhaust gas stream may be controlled through the operation of pump 24 and/or the injector 16, either or both of which may be controlled by a control unit, such as, for example, an electronic control unit (ECU) 26.

As illustrated, in FIG. 1, according to certain embodiments, a first temperature sensor 28a may be positioned at or around the inlet of the DOC 14. Additionally, a second and a third temperature sensor 28b, 28c may be positioned at or around the inlet and outlet, respectively, of the NPF 20. While FIG. 1 illustrates three temperature sensors, according to certain embodiments, additional temperature sensors may be employed, including, for example, a temperature sensor at or around the outlets of the engine 10 and/or DOC 14, or the inlet or outlet of the mixer 18, among others. Further the temperature sensors 28a-c in FIG. 1 may also be repositioned, such as, for example, the first sensor 28a being moved closer to the exhaust gas outlet of the engine 10.

Figure 2:
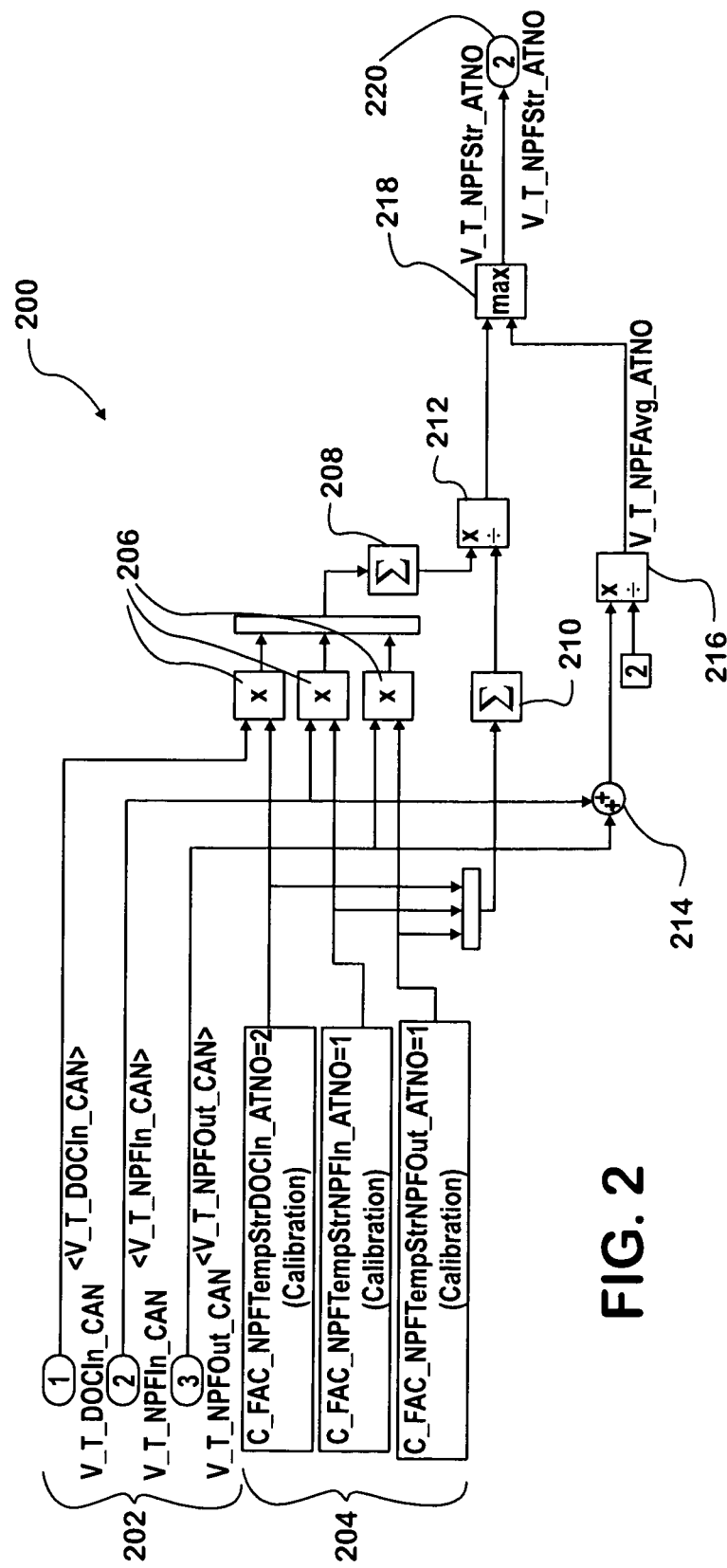
FIG. 2 is an exemplary algorithm or control logic for estimating a set-point for the amount of reductant to be stored on the SCR catalyst based on a predicted exhaust gas temperature.

FIG. 2 is an exemplary algorithm or control logic 200 for estimating a set-point for the amount of reductant to be stored on the SCR catalyst based on a predicted exhaust gas temperature. The logic 200 may be performed by a control unit, such as, for example, by the ECU 10. At step 202, a plurality of sensed temperature values are provided. For example, the temperature sensors 28a-c discussed above with respect to FIG. 1 may provide signals, such as voltages, to the ECU 26 that are indicative of the temperature of the exhaust gas at those sensed locations in the after-treatment system 12. The ECU 26 may be configured to determine the sensed temperature based on the information provided by the temperature sensors 28a-c.

More specifically, according to the embodiment of an after-treatment system 12 illustrated in FIG. 1, a first sensed temperature ("V_T_DOCin_CAN"), such as that provided by the first temperature sensor 28a that corresponds to a temperature at or around the inlet of the DOC 14 may be provided to and/or determined by the ECU 26 at step 202. Second and third sensed temperatures ("V_T_NPFin_CAN" and "V_T_NPFOut_CAN"), such as those provided by the second and third temperature sensors 28b, 28c at or around an inlet and outlet, respectively, of the NPF 20 may also be provided to and/or determined by the ECU 26 at step 202.

Figure 3:
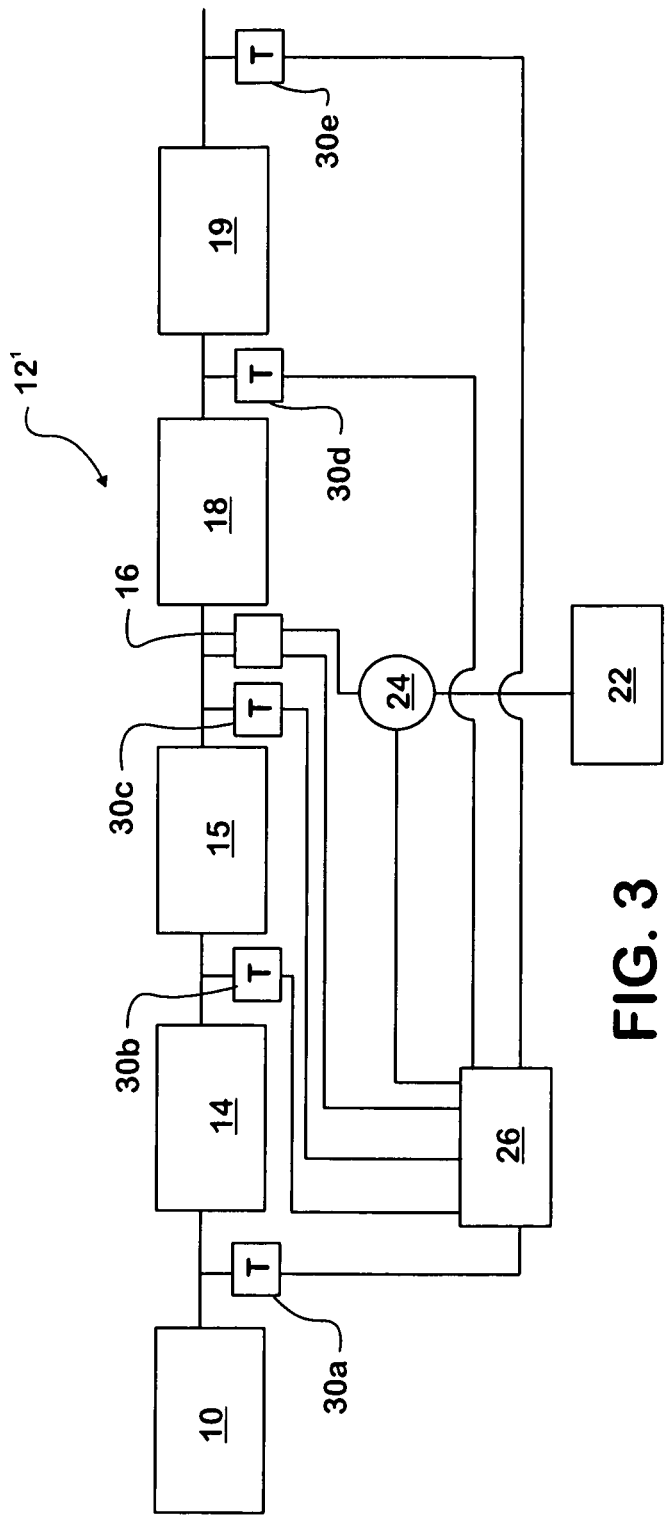
FIG. 3 illustrates an engine operably connected to an exemplary after-treatment system.

Although FIG. 2 illustrates the use of three sensed temperatures, a variety of other sensed temperatures, such as those previously discussed, may be used and/or included at step 202. For example, FIG. 3 illustrates an after-treatment system 12' that has a diesel particulate filter (DPF) 15 upstream of the injector 16 and an SCR catalyst 19 downstream of the mixer 18. As also shown, the after-treatment system 12' includes a five temperature sensors 30a-e positioned at various locations along the after-treatment system 12'. Thus, according to certain embodiments, some or all of the temperature sensors 30a-e may provide information to the ECU 26 that is used at step 202 in determining the set-point for the reductant storage level.

At step 204, the logic 200 may assign a total weight value to the temperatures provided at step 202. The total weight value assigned to each sensed temperature may depend on a variety of different factors. For example, the weight given to a temperature may be based on the location of the sensed temperature relative to the location of the SCR catalyst, the proximity of the sensed temperature to the engine 10 and/or the various thermal inertias within the after-treatment exhaust system 12. Such location based weighing may be used in an attempt to predict or estimate a future temperature of the exhaust gas that will be delivered to and/or encounter the SCR catalyst.

For example, in the embodiment illustrated in FIG. 2, the sensed temperature at or around the inlet of the DOC 14 may be given a total weight value of 2 ("C_FAC_NPTTEMPStrDOCIn_AT NO=2"), while the downstream sensed temperatures at or around the inlet and outlets of the NPF 20 may be given total weight values of 1 ("C_FAC_NPTTEMPStrNPFIn_AT NO=1" and "C_FAC_NPTTEMPStrNPFOut_AT NO=1"). By giving a larger total weight value to a sensed temperature that is furthest upstream of the SCR catalyst and/or in closer proximity to the engine 10, the logic 200 may be attempting to predict or estimate the temperature of the exhaust gas that will be, but may not have yet been, delivered to the SCR catalyst.

Such a prediction of the temperature of the exhaust gas that the SCR catalyst will be encountering may allow the ECU 26 to determine whether the set-point for the amount of reductant to be stored on the SCR catalyst should be adjusted and/or whether to adjust the amount of reductant being injected into the exhaust gas stream by the injector 16. Moreover, such prediction of temperature, such as a prediction of a temperature increase, may provide the ECU 26 the opportunity, if necessary, to adjust the reductant storage set-point of the SCR catalyst and allow for time to reduce the quantity of reductant stored on the SCR catalyst before the SCR catalyst encounters the elevated exhaust gas temperatures. Such adjustments in the amount of reductant being stored by the SCR catalyst may allow for time to prevent the release of excess reductant associated with a temperature related decrease in reductant storage capacity of the SCR catalyst, and thereby minimize or prevent the presence of excess reductant that may otherwise slip out of the after-treatment system and also reducing the waste of reductant.

According to certain embodiments, the total weight value given to the sensed temperatures may be a fixed value. However, according to other embodiments, the total weight value may be variable, such as, for example, based on operating conditions of the engine 10 and/or ambient conditions, among other factors. For example, the total weight value given to sensed temperatures may increase or decrease. Additionally, the total weight value associated with one or more sensed temperatures may increase or decrease regardless of whether the total weight value for other sensed temperatures increase, decrease, or remain the same. For example, during normal, steady operating conditions, the total weight value for the temperature sensed at or around the inlet of the DOC 14 may be similar to, or less than, the total weight value given to the temperatures sensed at or around the inlet or outlet of the NPF 20. However, the total weight value of the sensed temperature at or around the inlet of the DOC 14 may subsequently be increased as the engine load increases, such as when the vehicle associated with the engine changes from traveling on a relatively flat surface to climbing a relatively step incline. Additionally, while idling during cold starts, the total weight value for the temperature at or around outlet of the NPF 20 may increase as the temperature of the engine coolant increases while the total weight value for the temperature at or around the inlet of the DOC 14 remains the same.

At step 206, the total weight values from step 204 are applied to the temperatures provided at step 202. For example, if the sensed temperature at the inlet of the DOC 14 is 200° Celsius and the total weight value for that temperature is 2, then step 206 returns a weighted temperature value of 400° Celsius for that sensed temperature. Similarly, if the sensed temperatures at the inlet and outlets of the NPF 20 are 150° Celsius and 100° Celsius, respectively, and the total weight values for each of those temperatures is 1, then the weighted temperature values returned at step 206 for those sensed temperatures are 150° Celsius and 100° Celsius. At step 208, the weighted temperature values obtained at step 206 are summed together. Thus, in the present example, step 208 returns a total weighted temperature value of 650° Celsius. Further, at step 210, the total weight values applied to the sensed temperatures are summed together. Therefore, in the present example, as total weight values of 2, 1, and 1 were applied, step 210 provides a total weight value of 4.

At step 212, the total weighted temperature value from step 208 is divided by the total weight value from step 210 to provide an estimated temperature. Thus, in the present example, the total weighted temperature value of 650° Celsius is divided by a total weight value of 4 to provide an estimated temperature of 162.5° Celsius.

However, during certain operating conditions, the temperature sensed upstream of, and away from, the SCR catalyst, such as the temperature sensed at or around the inlet of the DOC 14, may be lower than the actual temperatures being encountered by the SCR catalyst. In such an event, predicting the exhaust gas temperature using the sensed exhaust gas temperature at such an upstream location, and/or giving relatively significant weight to such a sensed temperature, may result in the prediction of an exhaust gas temperature that is lower than the actual temperatures of the exhaust gases that will be encountering the SCR catalyst. Moreover, the resulting low temperature estimation may result in the ECU 26 increasing the set-point for the amount of reductant to be stored on the SCR catalyst and/or increasing the quantity of reductant dosed into the exhaust gas stream by the injector 16. However, such increases in the set-point and/or dosing levels based on a low exhaust gas temperature prediction may result in, based on the actual higher temperatures experience by the SCR catalyst, the SCR catalyst not being able to absorb and/or consume the increased level of reductant. In such a situation, the amount of reductant that may either actually or potentially slip through the after-treatment system 12, 12' may increase.

To avoid the potential for slippage/wastage of reductant based on low temperature predictions, according to certain embodiments, the logic 200 is configured to compare the estimated temperature from step 212 with the temperature of the exhaust gases that are encountering the SCR catalyst. Thus, at step 214, the inlet and outlet exhaust gas temperatures that are encountering the SCR catalyst are added together. For example, according to the embodiment illustrated in FIG. 3, the temperatures sensed by a fourth and fifth temperature sensors 30d, 30e may be added together, while the second and third temperature sensors 28b, 28c for the embodiment shown in FIG. 1 may be added together. With respect to the embodiment of FIG. 1, following the previously discussed example, if the inlet and outlet sensed temperatures are 150° Celsius and 100° Celsius, respectively, then step 214 would provide a summed temperature value of 250° Celsius. At step 216, the summed temperature value from 214 would be divided to provide an average temperature. For example, using the previous example in which two temperatures provided a summed temperature value of 250° Celsius at step 214, step 216 would return an average temperature of 125° Celsius.

At step 218, the average temperature ("V_T_NPFAvg_ATNO") from step 216 is compared to the estimated temperature from step 212. According to certain embodiments, step 218 would be configured to select the larger of either the average temperature or the estimated temperature to use in establishing the set-point for the quantity of reductant to be stored on the SCR catalyst. For example, using the previously discussed example, if the larger temperature ("V_T_NPFStr_ATNO") is to be selected, step 218 would select the estimated temperature of 162.5° Celsius over the average temperature of 125° Celsius.

At step 220, the selected temperature may be used by the ECU 26 to determine the set-point ("V_T_NPFStr_ATNO") for the storage of reductant on the SCR catalyst. According to certain embodiments, the temperature selected at step 218 may be used with a look-up table, chart, or other data that is accessible to the ECU 26 to establish the reductant storage set-point value. Thus, if the temperature of the exhaust gas is predicted to increase, using a reductant storage set-point value based on the predicted higher exhaust gas temperature may allow for reductant storage level of the SCR catalyst to be reduced accordingly so that if and when the exhaust gas temperature encountering the SCR catalyst does increase, the potential for excess reductant that may slip through the after-treatment system 12, 12' is minimized or eliminated.

The invention claimed is:

1. A method for predicting an exhaust gas temperature comprising:
   detecting a plurality of exhaust gas temperatures;
   applying, by a control unit, a weight value to the detected plurality of exhaust gas temperatures to determine a plurality of weighted temperature values, the weight value applied to at least one detected exhaust gas temperature being different than the weight value applied to at least one other detected exhaust gas temperature; and
   determining an estimated temperature corresponding to the plurality of weighted temperature values and the applied weight value;
   wherein the step of determining the estimated temperature comprises summing the plurality of weighted temperature values to determine a total weighted temperature value, summing the applied weight value to determine a total weight value, and dividing the total weighted temperature value by the total weight value;
   averaging at least two of the detected plurality of exhaust gas temperatures to determine an average temperature; and
   determining a set-point for the storage of a reductant on a catalyst using the higher temperature from the following temperatures: the estimated temperature or the average temperature.

2. A method for predicting an exhaust gas temperature comprising:
   detecting a plurality of exhaust gas temperatures;
   applying, by a control unit, a weight value to the detected plurality of exhaust gas temperatures to determine a plurality of weighted temperature values, the weight value applied to at least one detected exhaust gas temperature being different than the weight value applied to at least one other detected exhaust gas temperature; and
   determining an estimated temperature corresponding to the plurality of weighted temperature values and the applied weight value;
   wherein the step of determining the estimated temperature comprises summing the plurality of weighted temperature values to determine a total weighted temperature value, summing the applied weight value to determine a total weight value, and dividing the total weighted temperature value by the total weight value;
   further including the step of determining a set-point for the storage of a reductant on a catalyst based on the estimated temperature;
   wherein the step of detecting the plurality of exhaust gas temperatures includes detecting the temperature of exhaust gas entering a diesel oxidation catalyst;
   wherein the step of detecting the plurality of exhaust gas temperatures includes detecting the temperature of exhaust gases entering and exiting a housing containing a catalyst for a selective catalytic reduction system; and
   wherein the weight value applied to the temperature of the exhaust gas entering the diesel oxidation catalyst is greater than the weight value applied to the exhaust gas entering the housing and the weight value applied to the exhaust gas exiting the housing.

3. The method of claim 2, wherein the weight value applied to at least a portion of the plurality of exhaust gas temperatures is variable in response to engine operating conditions.

4. A method for predicting an exhaust gas temperature comprising:
   detecting the temperature of exhaust gasses entering a diesel oxidation catalyst;
   detecting the temperature of exhaust gases entering and exiting a housing containing a catalyst for a selective catalytic reduction;
   applying a weight value to the respective exhaust gas temperatures to determine a plurality of weighted temperature values, the weight value applied to the exhaust gas entering the diesel oxidation catalyst being different than the weight value applied to the exhaust gas entering and exiting the housing containing a catalyst for selective catalytic reduction;

determining, by a control unit, an estimated temperature using a first summed value representative of the plurality of weighted temperature values and a second summed value representative of the weight values that were applied to the detected plurality of sensed temperatures; and wherein the weight value applied to the temperature of the exhaust gas entering the diesel oxidation catalyst is greater than the weight value applied to the exhaust gas entering the housing and the weight value applied to the exhaust gas exiting the housing.

* * * * *